(12) United States Patent
Helmecke et al.

(10) Patent No.: US 9,342,656 B2
(45) Date of Patent: May 17, 2016

(54) USING EDS FOR EXTENDING A DESCRIPTION OF A LOADWARE UPDATE MECHANISM

(75) Inventors: Sven Helmecke, Möhrendorf (DE); Bernd Kalnischkies, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 1416 days.

(21) Appl. No.: 12/200,051

(22) Filed: Aug. 28, 2008

(65) Prior Publication Data

US 2010/0058040 A1 Mar. 4, 2010

(51) Int. Cl.
*G06F 9/24* (2006.01)
*G06F 19/00* (2011.01)

(52) U.S. Cl.
CPC .................................. *G06F 19/3412* (2013.01)

(58) Field of Classification Search
CPC .................................................. G06F 19/3412
USPC ............................................................. 710/8
See application file for complete search history.

(56) References Cited

U.S. PATENT DOCUMENTS

| 6,427,167 | B1 * | 7/2002 | Siedel ........................... 709/222 |
| 6,907,485 | B2 * | 6/2005 | White et al. ................... 710/260 |
| 7,031,798 | B2 * | 4/2006 | Brown et al. .................. 700/174 |
| 7,206,882 | B2 * | 4/2007 | White et al. ................... 710/110 |
| 7,274,693 | B1 * | 9/2007 | Kloth et al. .................... 370/389 |
| 2004/0231000 | A1 * | 11/2004 | Gossalia et al. ............... 725/132 |
| 2006/0200658 | A1 * | 9/2006 | Penkethman ..................... 713/2 |
| 2007/0080223 | A1 * | 4/2007 | Japuntich ....................... 235/439 |

* cited by examiner

*Primary Examiner* — Henry Tsai
*Assistant Examiner* — John Roche

(57) ABSTRACT

The invention refers to a computer-implemented method and system for loading a loadware file on a CANopen device. The CANopen device comprises an electronic data sheet, which is extended to comprise a load object. After reading the load object with the load parameters, the respective loadware file is located, selected and accessed. Accessing the loadware file is done by applying the read load parameters.

12 Claims, 3 Drawing Sheets

FIG 1   PRIOR ART   EDS

[1f50sub1]
ObjectType=7
ParameterName=Program_Area14
DataType=0x000F
AccessType=rw
PDOMapping=0

[1f50sub2]
ObjectType=7
ParameterName=Program_Area15
DataType=0x000F
AccessType=rw
PDOMapping=0

[1f51sub1]
ObjectType=7
ParameterName=ProgramControl1
DataType=0x0005
AccessType=rw
PDOMapping=0
DefaultValue0=0x00

FIG 3

EDS

```
[LoadwareInfo]
LWName=XYZ_LW.H86
LWChecksumAlgorithm=sum_of_inverted_bytes
LWGhecksumPosition=end_of_page
LWChecksumLengthBytes=4
LwFwSwitchDDO=ProgramControl
LWNumDelPages=2
LWDelPage1=0
LWDelPage2=1

[1f50sub1]
ParameterName=ProgramArea0
ObjectType=0x7
DataType=0x000F
LowLimit=196608
HighLimit=262143
DefaultValue=0
Access Type=rw
PDOMapping=0

[1f50sub2]
ParameterName=ProgramArea1
ObjectType=0x7
DataType=0x000F
LowLimit=262144
HighLimit=327679
DefaultValue=0
AccessType=rw
PDOMapping=0

[1f51sub1]
ParameterName=ProgramControl0
ObjectType=0x7
DataType=0x0005
LowLimit=0x00
HighLimit=0x3
DefaultValue=0x01
Access Type=rw
PDOMapping=0
```

USING EDS FOR EXTENDING A DESCRIPTION OF A LOADWARE UPDATE MECHANISM

FIELD OF THE INVENTION

The present invention is related to data processing in medical technology and in particular concerns a method for controlling peripheral devices in a medical technology environment; the invention also relates to a peripheral device and a system for communication with the peripheral device.

BACKGROUND OF THE INVENTION

Modern medical technology employs a large number of rather expensive and sophisticated echo apparatuses. Examples for such medical apparatuses are computer tomographs (CT), positron emission tomographs (PET) or other medical modalities. Other medical apparatuses include intensive care apparatuses. Those medical apparatuses are normally connected in a communication network in a modular fashion. Those medical apparatuses are connected via a suitable communication network. The peripheral devices are ranged for example to collect measurement data from patients. Examples of peripheral devices are injectors, respiration apparatuses, EKG monitors, amplifiers or devices for controlling respiration dating.

For the purposes of communication the peripheral devices are equipped with a specific protocol as a communication interface.

One of such protocol, specifying a communication interface is the so called CANopen interface, which is mainly used for embedded systems in automation. Each peripheral device or indeed any device complying with the standards specified in the CANopen protocol is called a CANopen device. The CANopen standard DS301 is a basic profile. In this standard there is provided a description of the communication functionality and of the device specific objects by means of an electronic data sheet (EDS). The EDS comprises background and meta-information relating to the device and is an electronic file, which usually is saved on the device itself. The CANopen standard is—referring to the OSI layering—the layer 7 communication protocol and is known particular from the field of automation technology but is also widely used in the field of medical technology.

According to the CANopen standard parameters and states of each CANopen device are described by means of objects arranged in tabular fashion in the EDS. The EDS for a particular CANopen device is normally available from the vendor. The data objects in the EDS are normally sufficient to describe how to access device parameters or settings. However, more complex accesses for example for the purposes of updating the CANopen device with loadware are not described sufficiently. The standard data objects in the EDS are not "rich enough" to describe such complex processes as a loadware update.

The CANopen device is normally provided with one or more microcontrollers onto which an application is loadable in order to enable the functionalities of the CANopen device.

As an example for an EDS file, known in the state of the art FIG. 1 shows parts of this file with relevant passages for example comprising an object having a number X1F50. This object comprises a number of sub objects which are shown in FIG. 1, for example the sub object 1f50sub1.

Generally, the first lines are specifying an object type a parameter name a data type, an access type and a PDO (process data object) mapping.

However, in the state of the art, there is an issue with those sub objects in that they do not supply sufficient details for example relating to which memory ranges are available for the update in the buffer of the loadware on the CANopen device. Therefore, in prior art systems the vendor had to supply further information on separate channels to enable an update of loadware. This process is, however, error-prone and non economical. For example, the vendor had to specify where the memory is located, which pages in memory are reusable in order to note the loadware onto and for example which one of sub objects is suitable for starting the up-loaded loadware.

SUMMARY OF THE INVENTION

Therefore, an object of the present invention is to provide a method of loading a loadware file on peripheral device having a CANopen interface. An electronic data sheet being associated with the peripheral device has been augmented to include a load object. The method comprises:
  reading the load object having load parameters from the augmented electronic data sheet;
  locating a loadware file by using the augmented electronic data sheet;
  upon accessing the located loadware file applying to read and load parameters to load the loadware file.

The electronic data sheet according to the present invention has been augmented by the load object in order to be rich enough to describe the loading process. A method according to the present invention therefore allows to automatize the loading of the loadware file in a safe manner. There are a number of advantages, resulting form this invention. Errors may be avoided, which are resulting from a failures concerning one of the updating processes or from a wrong memory information etc.

By loadware file is meant any piece of software suitable to enable functionalities of the CANopen peripheral device. Upgrading or updating software can therefore be considered synonymous to loadware file. Loading a loadware file may be construed as loading a new loadware, modifying an existing loadware file or deleting an old one and exchanging the same with a new one.

The electronic data sheet is a simple ASCII file or an XML file wherein a number of data objects representing parameters or parameter settings of the peripheral device are defined. According to the invention one of the objects is the load object.

The load object comprises a number of load parameters suitable to describe a loading process in sufficient detail to be automated. The load parameters comprise loadware initialisation information, memory page information and memory range information. The memory range information is related to a mapping into allocated the memory segments for loading the loadware file. The memory segments are units of the memory of the CANopen peripheral device. However, the memory segments may also relate to units of memory located outside the peripheral device with which the peripheral device is capable of communicating with.

According to an aspect of the present invention the method of loading a loadware file or an update of the loadware file respectively, comprises the step of:
  reading in the description for the loadware update form the EDS. This is done by means of accessing the load object of the EDS. The EDS might be stored on the CANopen peripheral device itself or alternatively or cumulatively might be stored on a separate module, which is provided with the device (a part might for example be stored on the device and the rest might be stored on another carrier). The relevant loadware file is selected and opened. Possibly format conversions are to be executed automatically (for example hex file in a binary).

According to another aspect of the present invention applying the respective loadware files with the respective accesses comprise:

switching into a bootloader (as a firmware context) by means of a write access to the object, having been defined in the EDS;

based on the memory page information erasing memory page content for one or more memory pages;

based on the memory range information allocating and/or loading ranges of memory in the memory pages;

executing the loadware by read accessing the allocated and/or loaded ranges of memory; wherein for the purpose of updating also a write access on the relevant objects listed in the EDS is possible.

According to one aspect of the present invention the loading of the loading file is executed automatically. The loading process is, for example, initiated by a user initiated signal.

According to an alternative embodiment of the present invention the execution of the loading of the loadware is initiated by the vendor sending an appropriate signal over a communication network to the peripheral device. Alternatively, the loading could be triggered by another instance together with an authentification signal form the user of the device or from the vendor.

According to an embodiment of the invention there are provided load conditions, which refer to more formal aspects of loading (time, format etc.). These conditions may be defined in a preparation phase, before loading and could be modified during use of the peripheral device. Further, these conditions could be supervised.

Until now the present invention has been described in relation to the method. Any aspects, features or advantages mentioned in this respect might also be applied to the system according to the invention and also to the computer readable medium and also to the peripheral unit according to the invention. With other words the system and the product might also be adapted to incorporate features, having been mentioned with respect to the description of the method according to the invention. Any functional feature refers to an apparatus feature, having the respective functionality. For example the step of "storing the load object" refers to a structural entity "storage medium adapted to store the load object".

Another object of the present invention is to provide a computer readable medium having computer readable instructions stored thereon for implementing the above method.

Another object of the present invention is to provide a system comprising a peripheral CANopen device on which device the loadware is to be loaded on. The system further comprises:

A storage having stored thereon the electronic data sheet to the alimented electronic data sheet including the load object having the load parameters;

A control unit communicatively coupled by means of a CANopen bus system to the peripheral device. The control unit is adapted to read in the load object and to locate the loader file by using the load parameters of the load object. The control unit is also adapted to apply the read and load parameters to load the loadware upon accessing the located loadware file.

The augmented electronic data sheet according to the present invention allows the control unit to load the loadware by means of a generic loading program or loading module. A development of the information in the electronic data sheet for precisely specifying the loading process can therefore in principal be coupled to the development of the generic loading program. Additional and possibly ambiguous documentation on the loading process is therefore no longer needed. The system according to the present invention therefore allows vendors to use a single generic loading program to control the loading process for a number of different CANopen peripheral devices. The loading parameters of the load object precisely specify (down to a mainly address level) the way in which the loadware is to be arranged on the memory of the peripheral device. The inventive system therefore allows the loading process to commence in the defined manner or matter the actual organisation of memory at the target that is the peripheral device.

Generic loading program is to be construed as any module executed on the control unit and suitable to control basic input/output operations on the peripheral device on which the loadware is to be loaded on.

The control unit is to be construed as for example a PC or a PDA or a laptop or another computer unit which a user can initiate and control the loading process by means of EDS. According to the invention the amended system allows to organize the loading process in manifold ways to fit local requirements. For example according to one alternative aspect of the present invention the electronic data sheet is stored in the peripheral device in a predetermined memory area. According to this aspect the vendor needs only to supply the peripheral device and tell the user whereon in memory the electronic data sheet is being located.

According to a yet alternative aspect of the present invention the electronic data sheet is not stored on the peripheral device it is rather stored externally on an external storage. According to this aspect of the present invention the control unit will have to communicate with the external storage to request and to retrieve the electronic data sheet thereon. According to this aspect of the present invention the vendor would supply a "naked" version of the peripheral device. If a user wishes to load the loadware onto the supplied peripheral device it is for example not necessary to access a backed or a website of the vendor at all.

The electronic data sheet is marked for the specific type of peripheral device. According to this aspect of the present invention the vendor is in the position to provide an updated version of the loadware at a minimum of logistic overhead.

The system according to the present invention also allows holding the loadware files themselves in different locations or to yet better fit local requirements. For example to one aspect of the present invention the files are resident on the control unit. According to this aspect the loadware files are straight "downloaded" on the control unit to the peripheral device.

According to another aspect of the present invention the loadware files are arranged on their repository external to the control unit. In this case the user will have to retrieve the loadware files from the repository before commencing the loading process. According to this aspect it is again for example the vendor's website on which the loadware files are available. In this case the user would simply use the browser in order to connect with the vendor's website to download the most recent loadware file he wishes to load onto the peripheral device.

According to yet another aspect of the present invention it is possible to provide the loadware file in a designated memory area of the peripheral device. According to this aspect the loadware files are "parked" in the designated area in first need to be loaded properly by means of the electronic sheet into areas of memory specified therein.

Any of the previous memory storage places for storing the electronic data sheet can be combined with any of before mentioned ways of storing the loadware files.

BRIEF DESCRIPTIONS OF THE DRAWINGS

FIG. 1 is a schematic diagram giving an overview of a prior arts electronic data sheet;

FIG. 3 is a schematic diagram of an electronic data sheet of an augmented electronic data sheet according to one aspect of the present invention;

DESCRIPTION OF THE PREFERRED EMBODIMENTS

Embodiments of a method for loading a loadware file on a peripheral device are described hereinafter. In the following description, meaning of specific details is given to provide a thorough understanding of embodiments of the invention. One skilled in the relevant art will recognize, however, that the invention can be practiced without one or more of the specific details, or with other methods, modules, entities etc. In other instances, well-known structures, computer related functions or operations are not shown or described in detail, as they will be understood by those skilled in the art.

Further, the method is described with respect to medical peripheral devices. However, it is apparent that also other categories or other typed of deviced, for example like automation devices might also be applied and processed, respectively.

In FIG. 1 there is shown a prior art electronic data sheet. According to the known data sheet it is not possible to have a specific loading of loadware files on a peripheral CANopen device CD. The old procedure is time consuming and error prone.

In contrast to this the invention suggests an augmented electronic data sheet EDS which is depicted in FIG. 3.

In FIG. 3 a first passage relates to "loadware info". This is a section with information relating to a loadware name, a check sum algorithm, position and a length. Further there is given a name of an object to start the loading. Further a number of pages is given, which might be deleted or which might be accesses via a write access ("LWNum-DelPages=2"). In section [1F50sub1] the electronic data sheet EDS is enlarged with a reference with respect to a parameter name and there is given a starting address for an object to be searched in the respective memory and there is given an ending address for the object to be searched in the respective memory (LowLimit/HighLimit). Although in the section [1F50sub1] there can be find these parameters (Low-Limit/HighLimit). In section [1F51sub1] there is also given further information concerning the parameter name as an object for starting the load ware.

Figure 2:
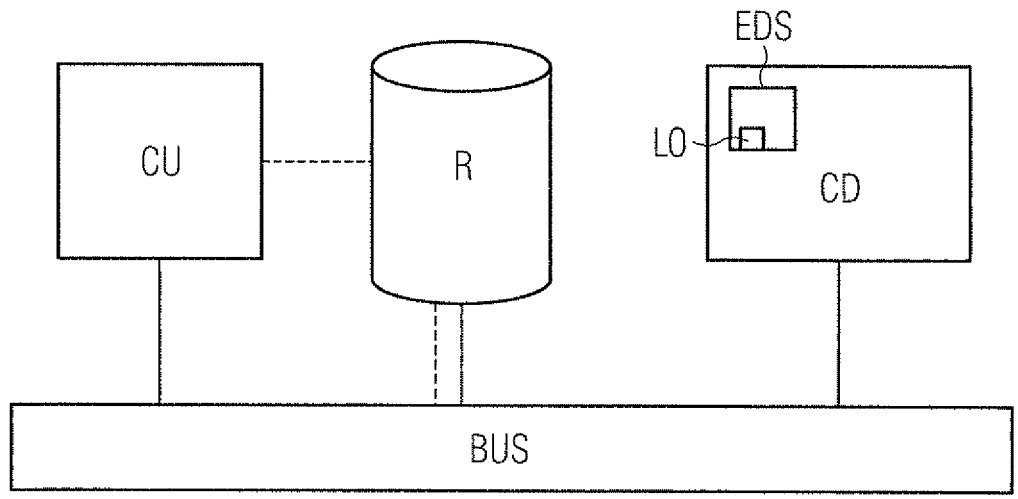
FIG. 2 is a schematic block diagram of a system for loading a loadware onto a peripheral device according to one aspect of the present invention.

In FIG. 2 there is shown a schematic bloc diagram of a system for loading a loadware file on one of a group of several CANopen devices CD according to one aspect of the present invention. A system comprises a control unit CU, which could be a personal computer, a laptop or a mobile device which is connected to a CANopen bus system BUS. The control unit CU and the CANopen device CD communicate over that CANopen bus BUS. The control unit CU also communicates with a repository R for storing information relating to the control unit CU and/or relating to the CANopen CD and particularly for loading an application software as so called loadware, on the CANopen device CD. The repository R might communicate over the CANopen bus BUS.

According to the invention the electronic data sheet EDS is extended to comprise a further object, namely a so/called load object LO. The load object Lo is to be used for a loading software application to the CANopen device CD.

However, alternatively it is also possible to associate the repository R to the control unit CU over another communication channel. This should be depicted in FIG. 2 with the dotted line from repository R to CAnopen bus BUS and with the dotted line from repository R to the control unit CU. In the latter case the repository R is associated to the control unit CU by a local area network (LAN), a wide area network (WAN), the internet or by other means of communication.

The CANopen device CD is typically associated to a large medical technology apparatus, such as a computer tomography, an ultrasound apparatus, a positron emission tomograph etc. The CANopen device CD can for example be an injector, a detection apparatus for respiration gating, an EKG monitor, internal or external lab equipments, internal or external sub switches, displays, anesthesia units, pulse oximeters etc. In the embodiment shown in FIG. 2 the interface between the respective elements of the system is a CANopen bus. However, also other standardized or proprietary interfaces might be used. However, also other elements with potential other interfaces can also be provided.

The electronic data sheet EDS is associated with the respective CANopen device CD. Normally, the electronic data sheet EDS is stored on the CANopen CD itself. However, it is also possible to store the electronic data sheet EDS in a separate data carrier which is in data communication with the respective CANopen device CD.

Figure 4:
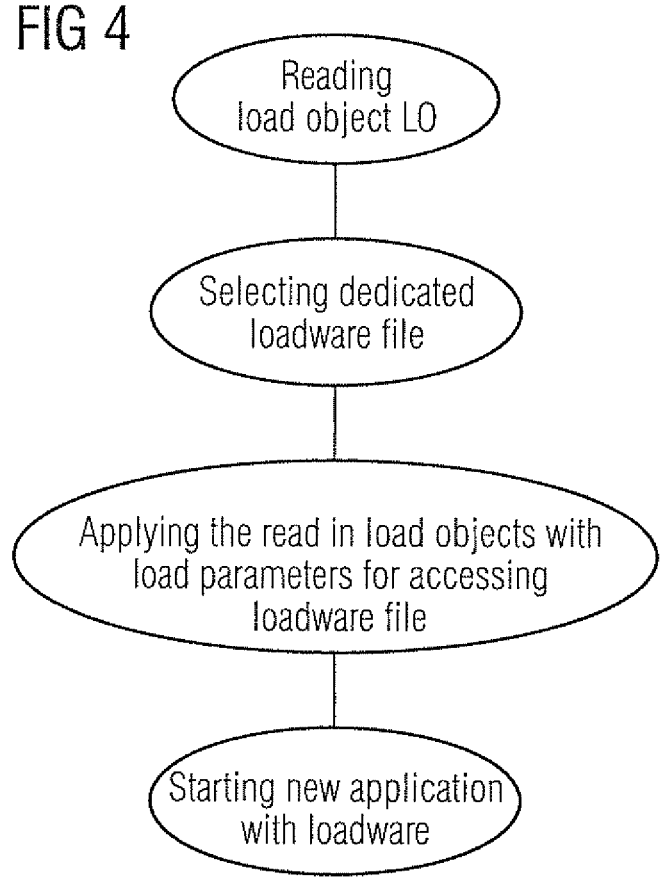
FIG. 4 is a basic flow chart of the method of loading the loadware file on a peripheral device according to one aspect of the present invention.

In FIG. 4 there is shown a basic flow chart with respect to the method of loading the loadware file on the CANopen device CD according to one aspect of the present invention. In a first step the load object LO is read in. The load object LO is part an electronic data sheet EDS according to the invention. Normally the control unit CU executes a read access to the load object LO stored on the electronic data sheet EDS, on the CANopen device CD over the CANopen bus system. In a second step the dedicated or related loadware file is selected. The loadware file is stored in the repository R. In a third step the read in load parameters are applied for accessing the loadware file LO. This is executed via write access from the control unit CU to the CANopen device CD with the respective files. In the fourth and last step the new application could be started with a new loadware on it. With this method provided by the invention a new loadware application could be started automatically without user interaction. All relevant data for loading the new software application are collected automatically from the respective information in the electronic data sheet EDS and in the repository R.

In a further preferred embodiment of the invention the method further comprises an additional step for informing a user whether or not the new loadware application could be loaded successfully. This could be signaled with respective optic or acoustic signal.

The invention can be realized in part or entirely by this software or hardware modules or by a combination of the same. Further the invention could be distributed among other physical products, in particular computer program products).

In addition while the foregoing description focused on the CANopen devices CD and on other specific features also other interfaces and alternative features maybe used without departing from the underlying principles of the invention.

Further, the method might be implemented in software, in coded form. Alternatively, it is possible to implement the method according to the invention in hardware or hardware modules. The hardware modules are then adapted to perform the functionality of the steps of the method. Furthermore, it is possible to have a combination of hardware and software modules.

These and other modifications can be made to the invention with regard of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

Accordingly, the scope and spirit of the invention should be judged in terms of the claims which follow.

What we claim is:

1. A computer-implemented method of loading a loadware file on a peripheral device having a CANopen interface by a control unit connected via a bus system the method comprising:
    providing an augmented electronic data sheet (EDS) stored on a peripheral device specifying a communication interface in accordance with CANopen standards, wherein the EDS includes standard data objects comprising a description of the communication functionality for the peripheral device and a description of device specific objects for the peripheral device describing how to access device parameters and settings, and wherein the EDS is further augmented with a load object for describing a loading process including a location of the loadware file for locating and selecting the loadware file;
    initiating a generic loading program of a control unit for loading a loadware file on a peripheral device;
    reading, by the control unit over a bus system, the load object having load parameters describing a load process for the loadware file from the augmented electronic data sheet (EDS) stored on the peripheral device, wherein the load object augments the EDS with load parameters comprising loadware initialization information, memory page information, and memory range information for loading the loadware file into allocated memory segments associated with the peripheral device;
    locating and selecting, by the control unit, the loadware file in accordance with the load parameters of the augmented electronic data sheet;
    loading the loadware file by the control unit into allocated memory segments associated with the peripheral device in accordance with the load parameters,
    wherein the generic loading program is used to control the loading process for different peripheral devices by having the load parameters stored in the EDS rather than in the generic loading program.

2. The computer-implemented method of claim 1, wherein the step of loading the loadware file into allocated memory segments associated with the peripheral device comprises:
    switching into a boot mode by write-accessing the load object;
    based on the memory page information, erasing memory page content from one or more memory pages;
    based on the memory range information, allocating and loading ranges of memory in the memory pages; and
    executing the loadware by write-accessing the allocated ranges of memory.

3. The method of claim 1, wherein the loading of the loadware file is executed automatically.

4. The method according to claim 1, wherein the location of the loadware file comprises memory starting and ending addresses for searching to locate the loadware file located at one of the control unit, a repository external to the control unit, or a designated memory area of the peripheral device.

5. The method according to claim 1, wherein the load object comprises load conditions, and wherein the load conditions may be defined, modified or monitored.

6. A non-transitory computer readable medium having computer-readable instructions for implementing the method according to claim 1.

7. A system for loading a loadware file on a peripheral device using a generic loading program comprising:
    a peripheral device, the peripheral device having a CANopen interface and the peripheral device being adapted to have loadware installed thereon;
    a storage associated with the peripheral device having stored thereon an electronic data sheet (EDS) specifying a communication interface in accordance with CANopen standards, wherein the electronic data sheet includes standard data objects comprising a description of the communication functionality for the peripheral device and a description of device specific objects for the peripheral device describing how to access device parameters and settings, and wherein the EDS is further augmented to include a load object for describing a load process, the load object having load parameters describing the load process for the loadware file, wherein the load object augments the EDS with load parameters comprising a location of the loadware file for locating and selecting the loadware file, loadware initialization information, memory page information, and memory range information for loading the loadware file into allocated memory segments associated with the peripheral device; and
    a control unit communicatively coupled by means of a CANopen bus system to the peripheral device, the control unit being adapted to execute a generic loading program that
    (a) reads in the load object,
    (b) locates the loadware file by using the load parameters of the load object; and
    (c) loads loadware file into allocated memory segments associated with the peripheral device in accordance with the load parameters;
    wherein the generic loading program is used to control the loading process for different peripheral devices by having the load parameters stored in the EDS rather than in the generic loading program.

8. The system according to claim 7 wherein the peripheral device comprises the storage having the augmented electronic data sheet stored thereon.

9. The system according to claim 7, wherein the storage is arranged externally of the peripheral device and wherein the control unit is adapted to communicate with the storage unit to read in the load object of the electronic data sheet.

10. The system according to claim 7, wherein the location comprises memory starting and ending addresses for searching to locate the loadware file wherein the loadware file is resident in the control unit.

11. The system according to claim 7, wherein the location comprises memory starting and ending addresses for searching to locate the loadware file wherein the loadware file is arranged in a repository external to the control unit and wherein the control unit is adapted to retrieve the loadware file from the repository.

12. A peripheral device adapted to have loadware installed thereon via a generic loading program of a control unit connected thereto via a bus system, wherein the generic loading program is used to control the loading process for different peripheral devices, the peripheral device comprising:
   an electronic data sheet (EDS) for the peripheral device stored thereon, the electronic data sheet specifying a communication interface in accordance with CANopen standards,
   wherein the electronic data sheet includes standard data objects comprising a description of the communication functionality for the peripheral device and a description of device specific objects for the peripheral device describing how to access device parameters and settings, and
   wherein the EDS is augmented to further comprise a load object describing a load process for the loadware file, wherein the load object augments the EDS with load parameters, the load parameters comprising a location of the loadware file for locating and selecting the loadware file, loadware initialization information, memory page information, and memory range information for loading the loadware file into allocated memory segments associated with the peripheral device,
   wherein the generic loading program is used to control the loading process for different peripheral devices by having the load parameters stored in the EDS rather than in the generic loading program.

* * * * *